(12) United States Patent
Storey et al.

(10) Patent No.: US 8,410,312 B2
(45) Date of Patent: Apr. 2, 2013

(54) FLUORINATION PROCESS OF ANILIDE DERIVATIVES AND BENZOTHIAZOLE FLUORINATE DERIVATIVES AS IN VIVO IMAGING AGENTS

(75) Inventors: Anthony Eamon Storey, Lincs (GB); Clare Louise Jones, Middlesex (GB); Denis Raymond Christophe Bouvet, Territoire de Belfort (FR); Nicolas Lasbistes, Buckinghamshire (GB); Steven Michael Fairway, Oslo (NO); Lorenzo Williams, Oslo (NO); Alexander Mark Gibson, Buckinghamshire (GB); Robert James Nairne, Herts (GB); Farhad Karimi, Canton, MA (US); Bengt Langstrom, Uppsala (SE)

(73) Assignees: GE Healthcare Limited, Buckinghamshire (GB); GE Healthcare AS, Oslo (NO)

( * ) Notice: Subject to any disclaimer, the term of this patent is extended or adjusted under 35 U.S.C. 154(b) by 780 days.

(21) Appl. No.: 12/063,470

(22) PCT Filed: Aug. 11, 2006

(86) PCT No.: PCT/GB2006/003009
§ 371 (c)(1),
(2), (4) Date: May 14, 2010

(87) PCT Pub. No.: WO2007/020400
PCT Pub. Date: Feb. 22, 2007

(65) Prior Publication Data
US 2010/0234611 A1 Sep. 16, 2010

(30) Foreign Application Priority Data
Aug. 12, 2005 (GB) .................... 0516564.2

(51) Int. Cl.
*C07C 211/46* (2006.01)
(52) U.S. Cl. ........................................ 564/306
(58) Field of Classification Search ........................ None
See application file for complete search history.

(56) References Cited

FOREIGN PATENT DOCUMENTS

| EP | 0015214 | 2/1980 |
|---|---|---|
| EP | 0664283 | 1/1995 |
| WO | 2004/083195 | 9/2004 |

OTHER PUBLICATIONS

Journal of Chromatography, 1990, vol. 507, pp. 293-302.
Forsyth, D.A. "Instinsic and equilibirium NMR isotope shift evidence for negative hyperconjugation" Journal of the American Chemical Society, vol. 108, 1986 pp. 2157-2161.
Zakrzewska, A., et.al. "4-fluoroanilines: synthesis and decomposition" Journal of Fluorine Chemistry, Elsevier Sequoia, Luasannew, CH, vol. 111, No. 1, Sep. 28, 2001, pp. 1-10.
Bergmann, Ernst, D. et.al., "An improved method for the preparation of fluorine-substituted aromatic amines" Journal of Organic Chemistry, 19, 1594-9 Coden: Joceah, 1954.
Zhang, Mei, et.al., "Synthesis of 3-methylkynurenic acid derivatives" Youji Huaxue, 24(4) 440-443 CODEN: YCHHDX.
Stavber, S. et.al., "New, mild, directed and high yield method for the fluorofunctionalisation of aromatic molecules" Journal of Fluorine Chemistry, vol. 54, No. 1-3, 1991 pp. 268-268.
Milner, D.J. "Fluoroaromatics from arylamines, a convenient one-pot conversion using nitrosonium tetrafluoroborate" Synthetic Communications, Taylor & Francis, Philadelphia, PA, vol. 22, No. 1, 1992, pp. 73-82.
GB0516564.2 search report dated Dec. 9, 2005.
PCT/GB2006/003009 Int'l Search Report and Written opinion dated Nov. 22, 2006.

*Primary Examiner* — Kamal Saeed
*Assistant Examiner* — Nyeemah A Grazier

(57) ABSTRACT

The invention relates to a process for preparation of a compound of formula (I): $R^1$ is selected from $C_{1-6}$alkyl, $C_{2-6}$alkenyl, and $C_{2-6}$alkynyl; which comprises: (i) reaction with fluoride, suitably [$^{18}$F]fluoride, of a corresponding compound of formula (II): wherein $R^2$ is selected from hydrogen, $C_{1-10}$alkyl, $C_{1-10}$haloalkyl, $C_{6-14}$aryl, $C_{6-14}$arylalkyl, —$(CH_2CH_2O)_q$—$CH_3$ wherein q is an integer of from 1 to 10; $R^1$ is as defined for the compound of formula (I); and $R^3$ is a leaving group. Certain novel precursors of formula (II) and radiopharmaceutical kits containing such precursors are also claimed.

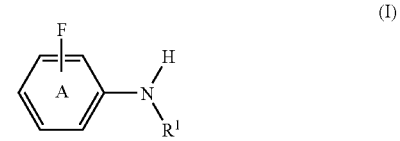

(I)

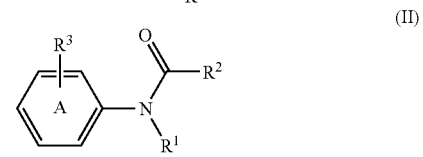

(II)

9 Claims, No Drawings

FLUORINATION PROCESS OF ANILIDE DERIVATIVES AND BENZOTHIAZOLE FLUORINATE DERIVATIVES AS IN VIVO IMAGING AGENTS

This application is a filing under 35 U.S.C. 371 of international application number PCT/GB2006/003009, filed Aug. 11, 2006, which claims priority to application number 0516564.2 filed Aug. 12, 2005, in Great Britain the entire disclosure of which is hereby incorporated by reference.

The present invention relates to novel processes for fluorination, particularly [$^{18}$F]fluorination of certain aromatic compounds, and to the novel precursors used in the process. The invention has particular utility for a class of benzothiazole derivatives which are known as in vivo imaging agents.

Fluorination of aromatic compounds may be performed via electrophilic reaction with molecular fluorine, however, electrophilic fluorination of aromatic compounds with fluorine is generally a poor and non-selective method. Different electrophilic fluorinating reagents prepared from molecular fluorine, such as $CH_3COOF$ "AcOF" have been developed but suffer several drawbacks. For [$^{18}$F]radiofluorination, the harsh conditions, and poor availability of electrophilic [$^{18}$F]fluorination methods, and the low specific activity of the products obtained mean that it is not a favoured approach for commercial production of [$^{18}$F]-labelled products. Nucleophilic fluorination methods, using fluoride are more commonly used. [$^{18}$F]Fluoride is a more widely available reagent than the electrophilic reagents and the products obtained are of higher specific activity which is advantageous in the field of in vivo imaging. Nucleophilic fluorination of aromatic rings, particularly those which are electron rich can be problematic. For example, nucleophilic fluorination of anilines, where the amino group adds to electron density of the aromatic ring is difficult to perform. The present invention provides a precursor suitable for nucleophilic fluorination to give a fluorinated aniline, which combines a number of beneficial effects including improved activation of the aromatic ring to fluorination, few steric effects on the fluorination reaction, and facile conversion to the fluorinated aniline product.

According to the invention, there is provided a process for preparation of a compound of formula (I):

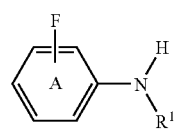
(I)

wherein phenyl ring A is optionally substituted by 1 to 4 substituents;
$R^1$ is selected from $C_{1-6}$alkyl, $C_{2-6}$alkenyl, and $C_{2-6}$alkynyl;
which comprises:
(i) reaction of a corresponding compound of formula (II):

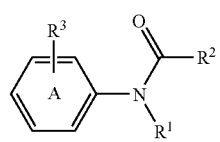
(II)

wherein ring A is optionally substituted as defined for the compound of formula (I);

$R^2$ is selected from hydrogen, $C_{1-10}$alkyl, $C_{1-10}$haloalkyl, $C_{6-14}$aryl, $C_{6-14}$arylalkyl, —$(CH_2CH_2O)_q$—$CH_3$ wherein q is an integer of from 1 to 10;
$R^1$ is as defined for the compound of formula (I); and
$R^3$ is a leaving group;
with fluoride to give a compound of formula (III)

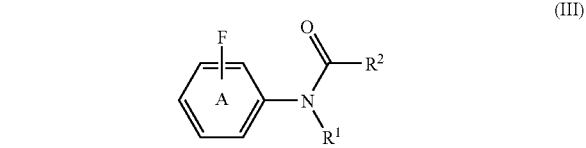
(III)

wherein $R^1$ and $R^2$ are as defined for the compound of formula (I) and phenyl ring A is substituted as defined for the compound of formula (I); followed by step (ii) and optionally step (iii) in any order
(ii) conversion of group —C(O)$R^2$ to hydrogen, suitably by hydrolysis
(iii) removal of any further protecting groups.

Phenyl ring A is optionally substituted by 1 to 4 organic substituents for example selected from fluoro, chloro, bromo, iodo, cyano, nitro, —R, —OR, —OC(O)R, —C(O)R, —SR, —NR$_2$, —C(O)NR$_2$ wherein R at each occurrence is selected from $C_{1-6}$alkyl, $C_{2-6}$alkenyl, $C_{2-6}$alkynyl, $C_{1-6}$alkoxy-$C_{1-6}$alkyl, $C_{1-6}$haloalkyl, $C_{2-6}$haloalkenyl, $C_{2-6}$haloalkynyl, $C_{1-6}$haloalkoxy-$C_{1-6}$alkyl, $C_{5-12}$aryl, $C_{5-12}$ hetaryl wherein said aryl and hetaryl substituents may be further substituted by the non-aryl and non-hetaryl substituents listed for phenyl ring A, and a protected derivative of any thereof.

$R^2$ in the compound of formula (II) is selected from hydrogen, $C_{1-10}$alkyl (more suitably $C_{1-6}$alkyl, yet more suitably methyl), $C_{1-10}$haloalkyl (more suitably $C_{1-6}$haloalkyl such as $C_{1-6}$-fluoroalkyl, for example trifluoromethyl), $C_{6-14}$aryl (suitably phenyl), $C_{6-14}$arylalkyl (suitably phenyl-$C_{1-4}$alkyl, for example benzyl), and —$(CH_2CH_2O)_q$—$CH_3$ wherein q is an integer of from 1 to 10. Compounds of formula (II) wherein $R^2$ is $C_{4-10}$alkyl or —$(CH_2CH_2O)_q$—$CH_3$ wherein q is an integer of from 1 to 10 may be used in the process where it is desirable to increase solubility of the compound of formula (II) and as such these compounds and the process according to the invention using them, form separate aspects of the invention. Preferably, $R^2$ in the compound of formula (II) is selected from hydrogen and $C_{1-6}$alkyl, more preferably, $R^2$ is hydrogen.

$R^3$ in the compound of formula (II) is a leaving group, capable of being displaced by fluoride and is suitably selected from
nitro,
—$N_2^+$,
chloro,
bromo,
iodo,
—$NR^4(C_{1-6}alkyl)_2^+$ wherein $R^4$ is $C_{1-6}$alkyl or a group of formula (X):

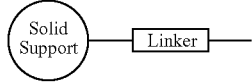
(X)

—OSO$_2$R$^5$ wherein R$^5$ is selected from C$_{1-6}$alkyl, C$_{1-6}$haloalkyl such as C$_{1-6}$ perfluoroalkyl, aryl such as phenyl or tolyl (for example, para-tolyl), and a group of formula (X) as defined above; and

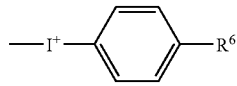

wherein R$^6$ is selected from hydrogen, C$_{1-6}$alkyl, halo, nitro, and a group of formula (X) as defined above.

R$^3$ in the compound of formula (II) is suitably selected from:
nitro,
—N$_2^+$,
chloro,
bromo,
iodo,
—NR$^4$(C$_{1-6}$alkyl)$_2^+$ wherein R$^4$ is C$_{1-6}$alkyl
—OSO$_2$R$^5$ wherein R$^5$ is selected from C$_{1-6}$alkyl, C$_{1-6}$haloalkyl such as C$_{1-6}$ perfluoroalkyl, aryl such as phenyl or tolyl (for example, para-tolyl); and

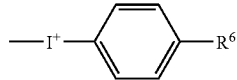

wherein R$^6$ is selected from hydrogen, C$_{1-6}$alkyl, halo, and nitro.

In one particular aspect of the invention, R$^3$ is nitro.

In the process according to the invention, use of compounds of formula (II) in which R$^3$ comprises a group of formula (X) allows the fluorination to be performed in solid-phase which may simplify purification of the fluorinated product as any unreacted precursor remains bound to the solid-support and may be removed from the solution-phase product by filtration.

In the group of formula (X), the Solid Support may be any suitable solid-phase support which is insoluble in any solvents to be used in the process but to which the Linker and/or compound of formula (II) can be covalently bound. Examples of suitable Solid Support include polymers such as polystyrene (which may be block grafted, for example with polyethylene glycol), polyacrylamide, or polypropylene or glass or silicon coated with such a polymer. The Solid Support may be in the form of small discrete particles such as beads or pins, or as a coating on the inner surface of a cartridge or on a microfabricated vessel.

In the group of formula (X), the Linker may be any suitable organic group which serves to space the reactive site sufficiently from the solid support structure so as to maximise reactivity. Suitably, the Linker comprises zero to four aryl groups (suitably phenyl) and/or a C$_{1-6}$ alkyl or C$_{1-6}$haloalkyl (suitably C$_{1-6}$ fluoroalkyl), and optionally one to four additional functional groups such as amide or sulphonamide groups. Examples of such linkers are well known to those skilled in the art of solid-phase chemistry, but include:

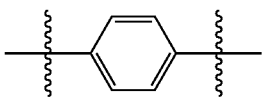

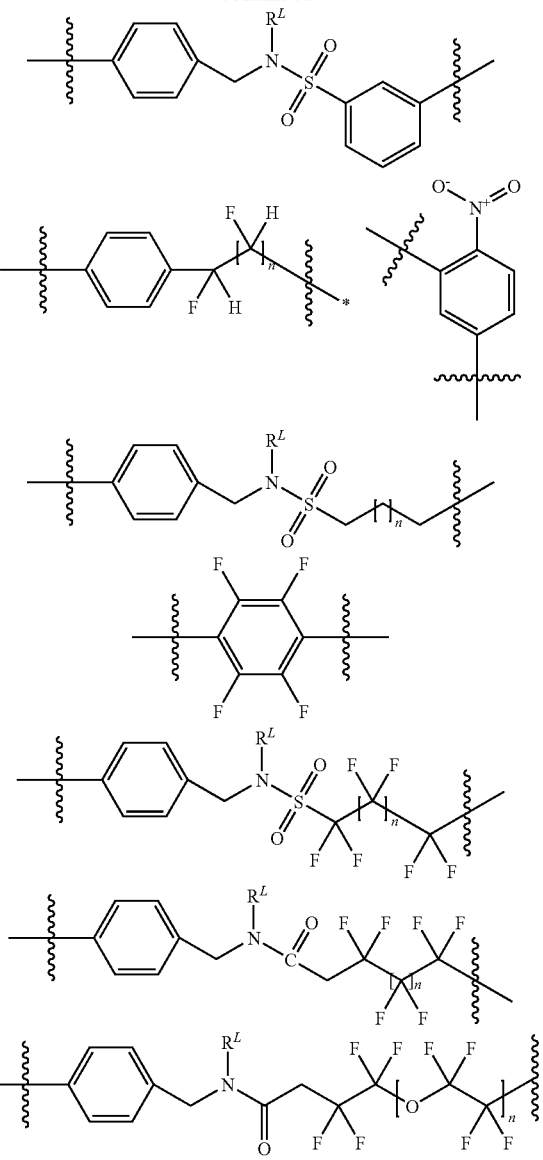

wherein at each occurrence, n is an integer of 0 to 3 and R$^L$ is hydrogen or C$_{1-6}$alkyl.

Step (i) of the process according to the invention i.e. reaction of a compound of formula (II) with fluoride, suitably [$^{18}$F]fluoride may be effected using a fluoride source such as NaF, KF, CsF, tetraalkylammonium fluoride, or tetraalkylphosphonium fluoride, suitably an [$^{18}$F]fluoride source such as Na$^{18}$F, K$^{18}$F, Cs$^{18}$F, tetraalkylammonium [$^{18}$F]fluoride (for example, tetrabutylammonium [$^{18}$F]fluoride), or tetraalkylphosphonium $^{18}$F fluoride. To increase the reactivity of the fluoride, a phase transfer catalyst such as an aminopolyether or crown ether, for example, 4,7,13,16,21,24 hexaoxa-1,10-diazabicyclo[8,8,8] hexacosane (Kryptofix 2.2.2) may be added and the reaction performed in a suitable solvent. These conditions give reactive fluoride ions. Optionally, a free radical trap may be used to improve fluorination yields, as described in WO 2005/061415. The term "free radical trap" is defined as any agent that interacts with free radicals and inactivates them. A suitable free radical trap for this purpose may be selected from 2,2,6,6-Tetramethylpiperidine-N-Oxide (TEMPO), 1,2-diphenylethylene (DPE), ascorbate, para-amino benzoic acid (PABA), α-tocopherol, hydroquinone, di-t-butyl phenol, β-carotene and gentisic acid. Preferred free radical traps for use in the process of the invention are TEMPO and DPE, with TEMPO being most preferred.

The treatment with fluoride, suitably [$^{18}$F]fluoride in step (i) may be effected in the presence of a suitable organic solvent such as acetonitrile, dimethylformamide, dimethylsulphoxide, dimethylacetamide, tetrahydrofuran, dioxan, 1,2 dimethoxyethane, sulpholane, N-methylpyrrolidininone, or in an ionic liquid such as an imidazolium derivative (for example 1-ethyl-3-methylimidazolium hexafluorophosphate), a pyridinium derivative (for example, 1-butyl-4-methylpyridinium tetrafluoroborate), a phosphonium compound, or tetralkylammonium compound at a non-extreme temperature, for example, 15° C. to 180° C., preferably at elevated temperature, such as 80° C. to 150° C., for example around 120° C. The organic solvent is suitably anhydrous, but in some cases may contain low levels of water.

In one aspect of the invention, the fluoro group in the compound of formula (I) is [$^{18}$F]fluoro and the fluoride used in step (i) of the process is [$^{18}$F]fluoride. There is particular need for novel radiofluoridation methods, especially for radiofluoridation of electron rich aromatic systems.

Step (ii) in the process, i.e. conversion of group —C(O)R$^2$ to hydrogen, is suitably effected by acid or base hydrolysis, using an organic or inorganic acid, at non-extreme temperature, for example ambient temperature to reflux temperature. The reaction may be performed in presence of an aqueous solvent or organic solvent, for example C$_{1-4}$alcohol such as methanol or ethanol or acetonitrile, or a mixture of aqueous and organic solvents.

Suitable acids used in step (ii) include hydrobromic, trifluoroacetic, phosphoric, and hydrochloric.

Suitable bases used in step (ii) include sodium hydroxide or potassium hydroxide. Use of sodium hydroxide in an organic solvent such as acetonitrile, at elevated temperature for example around 100° C. may give rise to good radiochemical yields and facilitate purification of the fluorinated product.

Alternative bases used in step (ii) include non-nucleophilic bases such as sodium hydride. This method gives rise to good radiochemical yields and also facilitates purification of the fluorinated product. Treatment with sodium hydride may be performed in a suitable aprotic solvent such as acetonitrile or propionitrile and at elevated temperature such as 40° C. to 120° C., typically around 100° C. Sodium borohydride, lithium borohydride, and lithium aluminium hydride are also suitable bases for use in step (ii).

As would be apparent to the person skilled in the art, it is sometimes necessary to use protecting group strategies to prevent unwanted side-reactions during organic synthesis. Examples of such strategies may be found in Protecting Groups in Organic Synthesis, Theodora W. Greene and Peter G. M. Wuts, published by John Wiley & Sons Inc. which describes methods for incorporating and removing protecting groups. To avoid unnecessary synthetic steps, it is particularly beneficial if any protecting groups remaining in the compound of formula (III) are removed under the conditions of step (ii) so as to avoid a separate deprotection step.

As used herein, the term "alkyl" used alone or as part of another group means a saturated straight or branched chain hydrocarbon radical, such as methyl, ethyl, propyl, iso-propyl, butyl, iso-butyl, tert-butyl, n-pentyl, or n-hexyl.

As used herein, the term "alkenyl" used alone or as part of another group means an unsaturated straight or branched chain hydrocarbon radical comprising at least one carbon to carbon double bond, such as ethenyl, propenyl, iso-propenyl, butenyl, iso-butenyl, tert-butenyl, n-pentenyl, and n-hexenyl.

As used herein, the term "alkynyl" used alone or as part of another group means an unsaturated straight or branched chain hydrocarbon radical comprising at least one carbon to carbon triple bond, such as ethynyl, propynyl, iso-propynyl, butynyl, iso-butynyl, tert-butynyl, n-pentynyl, and n-hexynyl.

As used herein, the term "halo" used alone or as part of another group means fluoro, chloro, bromo, or iodo.

As used herein, the term "aryl" used alone or as part of another group means an aromatic hydrocarbon single ring or fused ring system, such as phenyl or naphthyl.

As used herein, the term "hetaryl" used alone or as part of another group means an aromatic hydrocarbon single ring or fused ring system which additionally comprises 1 or more heteroatoms selected from sulphur, nitrogen, and oxygen, such as pyridyl, thiophenyl, benzothiazolyl, benzoxazolyl, or furyl.

The process according to the invention has particular utility for synthesis of compounds of formula (I) in which R$^1$ is C$_{1-6}$alkyl, and particularly methyl, thus the processes wherein R$^1$ in the compounds of formula (I), (II), (III) is C$_{1-6}$alkyl, and particularly methyl form a separate aspect of the invention.

The process according to the invention is particularly useful when the fluoro group in the compound of formula (I) is ortho or para to the group —N(R$^1$)C(O)R$^2$ as the —N(R$^1$)C(O)R$^2$ positioned ortho or para to R$^3$ in the corresponding compound of formula (II) may activate R$^3$ to nucleophilic displacement by fluoride. Preferably, the fluoro group in the compound of formula (I) is ortho to the group —N(R$^1$)C(O)R$^2$ and the group R$^3$ in the corresponding compound of formula (II) is ortho to the group —N(R$^1$)C(O)R$^2$.

Certain compounds of formula (I) are known to have use in diagnostic and therapeutic methods, for example the benzothiazole derivatives described for in vivo imaging of amyloid according to the methods described in WO 02/16333 and WO2004/083195. The methods previously described for preparing these benzothiazole derivatives, although suitable for preparing small amounts of the compounds, suffer from poor radiochemical yields and poor reproducibility such that there exists a need for improved processes for their preparation, particularly for a commercial setting. As mentioned above, nucleophilic fluorination of an aromatic ring can be problematic where the ring is electron rich. In the compounds of formula (Ia) and (Ib) below, the substitution pattern makes the aromatic ring difficult to fluorinate. Attempts to design a suitable precursor for fluorination, which was stable, could be fluorinated in good yield, and could then be readily converted to final product, were problematic as demonstrated below in Example 3. Thus, in a further aspect of the invention, there is provided a process for preparation of a compound of formula (Ia):

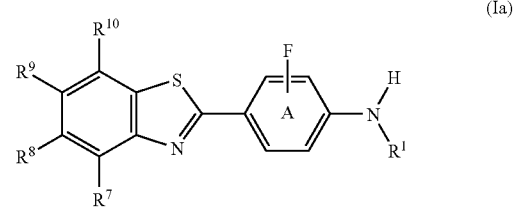

wherein
R$^1$ is selected from C$_{1-6}$alkyl, C$_{2-6}$alkenyl, and C$_{2-6}$alkynyl, R$^7$, R$^8$, R$^9$, and R$^{10}$ are each independently selected from hydrogen, fluoro, chloro, bromo, iodo, C$_{1-6}$alkyl, C$_{2-6}$alkenyl, C$_{2-6}$alkynyl, (CH$_2$)$_m$OR$^{11}$ (wherein m=1, 2, or 3), CF$_3$, CH$_2$—CH$_2$Y, O—CH$_2$—CH$_2$Y, CH$_2$—CH$_2$—CH$_2$Y, O—CH$_2$—CH$_2$—CH$_2$Y (wherein Y is selected from fluoro, chloro, bromo, and iodo), CN, (C=O)—R$^{11}$, N(R$^{11}$)$_2$, NO$_2$, (C=O)N(R$^{11}$)$_2$, O(CO) R$^{11}$, SR$^{11}$, COOR$^{11}$, R$_{ph}$, CR$^{11}$=CR$^{11}$—R$_{ph}$, CR$^{11}$$_2$—CR$^{11}$$_2$—R$_{ph}$ (wherein R$_{ph}$ represents an unsubstituted or substituted phenyl group with the phenyl substituents being chosen from any of the non-phenyl substituents defined for R$^7$ to R$^{10}$ and wherein R$^{11}$ is H or C$_{1-6}$alkyl) and a protected derivative of any thereof; and
phenyl ring A is substituted by 1 to 3 substituents being chosen from any of the non-phenyl substituents defined for R$^7$ to R$^{19}$;
which comprises:
(i) reaction of a corresponding compound of formula (IIa):

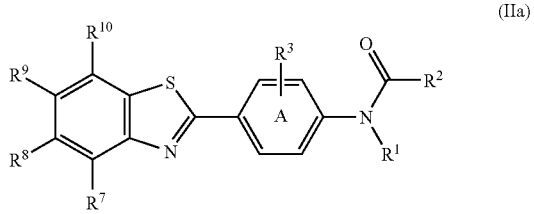

(IIa)

wherein
R$^1$ is defined for the compound of formula (Ia),
phenyl ring A is substituted as defined for the compound of formula (Ia); and
R$^2$ is selected from hydrogen, C$_{1-10}$alkyl, C$_{1-10}$haloalkyl, C$_{6-14}$aryl, C$_{6-14}$arylalkyl, —(CH$_2$CH$_2$O)$_q$—CH$_3$ wherein q is an integer of from 1 to 10;
R$^3$ is a leaving group as defined for the compound of formula (II);
R$^7$, R$^8$, R$^9$, and R$^{10}$ are as defined for the compound of formula (Ia);
with fluoride to give a compound of formula (IIIa)

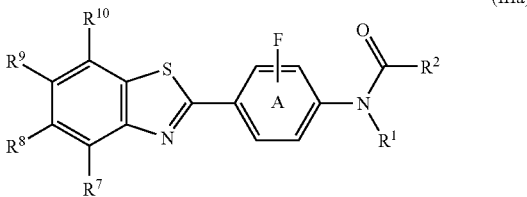

(IIIa)

wherein R$^1$ and R$^2$ are as defined for the compound of formula (IIa), phenyl ring A is substituted as defined for the compound of formula (Ia);
R$^7$, R$^8$, R$^9$, and R$^{10}$ are as defined for the compound of formula (Ia); followed by step (ii) and optionally step (iii) in any order
(ii) conversion of group —C(O)R$^2$ to hydrogen, suitably by hydrolysis
(iii) removal of any further protecting groups.

In the compounds of formula (Ia), (IIa), and (IIIa) and the corresponding process according to the invention, R$^7$, R$^8$, R$^9$, and R$^{10}$ are suitably selected from hydrogen, hydroxy, —NO$_2$, —CN, —COOR$^{11}$, —OCH$_2$OR$^{11}$ (wherein R$^{11}$ is selected from hydrogen and C$_{1-6}$alkyl), C$_{1-6}$alkyl, C$_{2-6}$alkenyl, C$_{2-6}$alkynyl, C$_{1-6}$alkoxy, halo, and a protected derivative of any thereof. Suitable protected derivatives of substituents R$^7$, R$^8$, R$^9$, and R$^{10}$ would be apparent to the person skilled in the art, and are described in Theodora W. Greene and Peter G. M. Wuts as referenced hereinbefore. For example, when R$^7$, R$^8$, R$^9$, or R$^{10}$ is hydroxy, the hydroxy function is suitably protected as a C$_{1-6}$alkoxymethoxy group such as ethoxymethoxy or methoxymethoxy.

One class of preferred compounds of formula (Ia) for use in in vivo imaging of amyloid are those of formula (Ib)

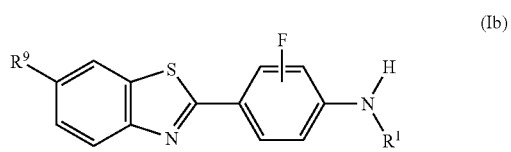

(Ib)

wherein R$^1$ is selected from C$_{1-6}$alkyl, C$_{2-6}$alkenyl, and C$_{2-6}$alkynyl; and R$^9$ is selected from hydroxy, —NO$_2$, —CN, —COOR$^{11}$, —OCH$_2$OR$^{11}$ (wherein R$^{11}$ is selected from hydrogen and C$_{1-6}$alkyl), C$_{1-6}$alkyl, C$_{2-6}$alkenyl, C$_{2-6}$alkynyl, C$_{1-6}$alkoxy, halo, and a protected derivative of any thereof, and is preferably selected from hydroxy, C$_{1-6}$alkoxy, and a protected derivative of any thereof, and is more preferably selected from hydroxy, methoxy, and a protected derivative of either thereof. Therefore, according to one preferred aspect of the invention there is provided a process for preparation of a compound of formula (Ib):

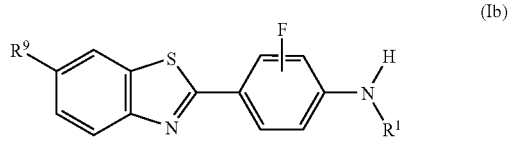

(Ib)

wherein
R$^1$ is selected from C$_{1-6}$alkyl, C$_{2-6}$alkenyl, and C$_{2-6}$alkynyl;
R$^9$ is selected from hydroxy, —NO$_2$, —CN, —COOR, —OCH$_2$OR, C$_{1-6}$alkyl, C$_{2-6}$alkenyl, C$_{2-6}$alkynyl, C$_{1-6}$alkoxy, halo, and a protected derivative of any thereof, and is preferably selected from hydroxy, C$_{1-6}$alkoxy, and a protected derivative of any thereof, and is more preferably selected from hydroxy, methoxy, and a protected derivative of either thereof;
which comprises:
(i) reaction of a corresponding compound of formula (IIb):

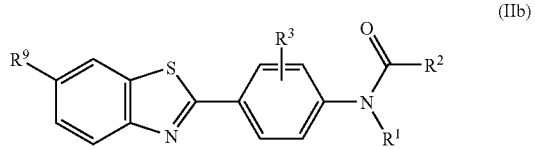

(IIb)

wherein R$^1$ is selected from C$_{1-6}$alkyl, C$_{2-6}$alkenyl, and C$_{2-6}$alkynyl, and R$^2$ is selected from hydrogen, C$_{1-10}$alkyl, C$_{1-10}$haloalkyl, C$_{6-14}$aryl, C$_{6-14}$arylalkyl, —(CH$_2$CH$_2$O)$_q$—CH$_3$ wherein q is an integer of from 1 to 10;

$R^3$ is a leaving group as defined for the compound of formula (II);
$R^9$ is as defined for the compound of formula (Ib);
with fluoride to give a compound of formula (IIIb)

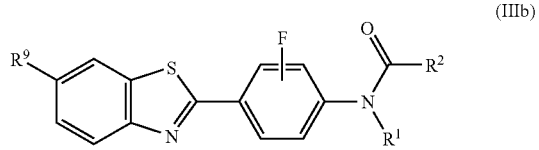

(IIIb)

wherein $R^1$ and $R^2$ are as defined for the compound of formula (IIb);
$R^9$ is as defined for the compound of formula (Ib); followed by step (ii) and optionally step (iii) in any order
(ii) conversion of group —C(O)$R^2$ to hydrogen, suitably by hydrolysis
(iii) removal of any further protecting groups in substituent $R^9$.

Compounds of formulae (IIa) and (IIb) as defined above are important precursors, useful for the preparation of in vivo imaging agents and therefore form further aspects of the invention.

Preferred precursors of formula (IIa) and (IIb) include those where $R^2$ is hydrogen or $C_{1-6}$alkyl, suitably methyl, more suitably $R^2$ is hydrogen; $R^1$ is $C_{1-6}$alkyl, suitably methyl; of these precursors in which $R^3$ is nitro may have particular utility. Compounds of formula (IIa) and (IIb) in which $R^9$ is hydroxy or $C_{1-6}$alkoxy or a protected derivative thereof may also have particular utility. One preferred such precursor is 2-[3-nitro-4-(methylformylamino)phenyl]-6-ethoxymethoxy-benzothiazole.

Conveniently, a precursor of formula (II), (IIa), or (IIb) could be provided as part of a kit, for example for use in a radiopharmacy. The kit may contain a cartridge which can be plugged into a suitably adapted automated synthesiser. The cartridge may contain, apart from the precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers requirements for radioactive concentration, volumes, time of delivery etc. Conveniently, all components of the kit are disposable to minimise the possibilities of contamination between runs and may be sterile and quality assured.

The invention further provides a radiopharmaceutical kit for the preparation of an $^{18}$F-labelled tracer for use in PET, which comprises:
(i) a vessel containing a compound of formula (II), (IIa), or (IIb); and
(ii) means for eluting the vessel with a source of $^{18}$F$^-$;
(iii) an ion-exchange cartridge for removal of excess $^{18}$F$^-$; and optionally
(iv) a cartridge for deprotection of the resultant product of formula (I), (Ia), or (Ib).

The invention further provides a cartridge for a radiopharmaceutical kit for the preparation of an $^{18}$F-labelled tracer for use in PET which comprises:
(i) a vessel containing a compound of formula (II), (IIa), or (IIb); and
(ii) means for eluting the vessel with a source of $^{18}$F$^-$.

Compounds of formula (II), (IIa), and (IIb) may be prepared from commercially available starting materials or using starting materials described in WO 02/16333 and WO2004/083195, by standard methods of organic chemistry, for example by the methods described below and in the examples.

Compounds of formula (II), (IIa), and (IIb) wherein $R^3$ is nitro may be prepared by methods analogous to those described in Example 1.

Compounds of formula (II), (IIa), and (IIb) wherein $R^3$ is chloro, bromo, iodo, tosylate, or an iodonium salt, may be prepared by methods analogous to those shown in Schemes 1 to 4 respectively.

In Schemes 1 to 6, $R^2$ is as defined for a compound of formula (I) above, R in scheme 1 is an alkyl or aryl substituent, Ac is acyl, Ts is tosyl, NaHDMS is sodium hexamethyldisilazide, TFA is trifluoroacetic acid, Pd$_2$dba$_3$ in Scheme 6 is tris-(dibenzylideneacetone)dipalladium(0) and the other abbreviations are as defined in the Examples.

Scheme 1

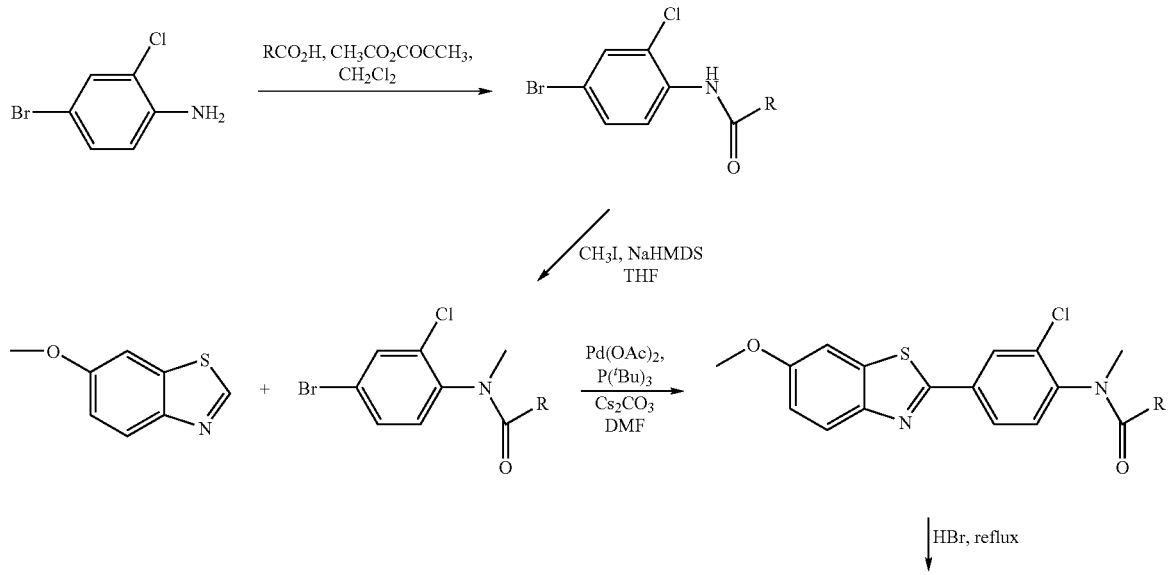

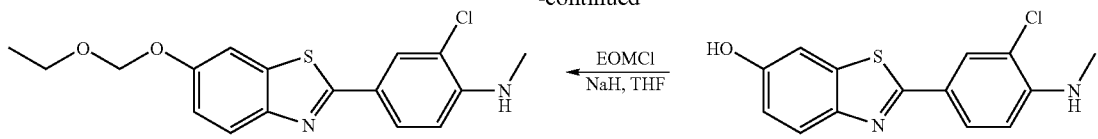
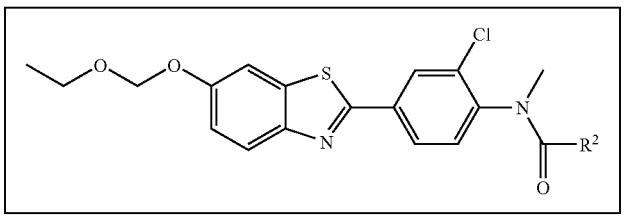
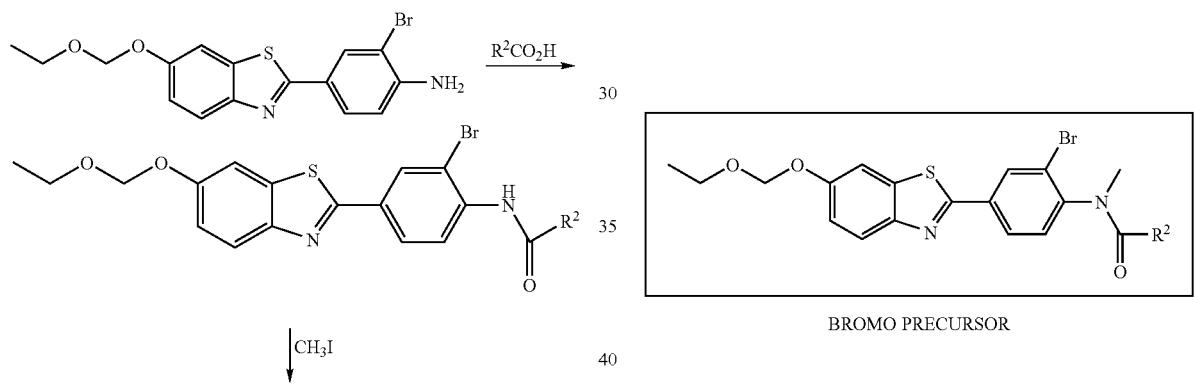
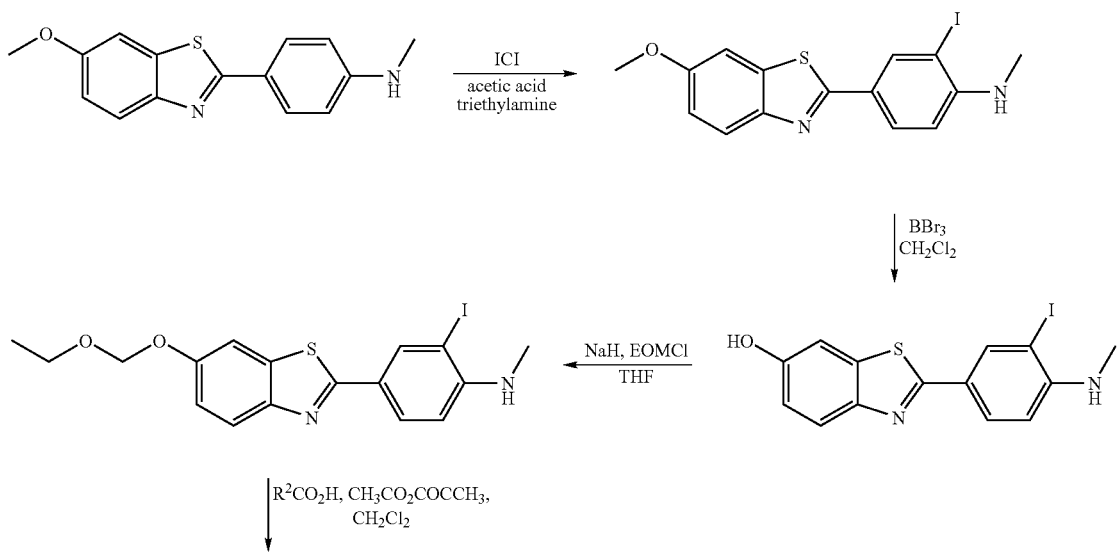

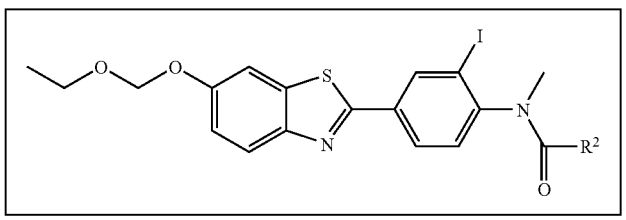
IODO PRECURSOR
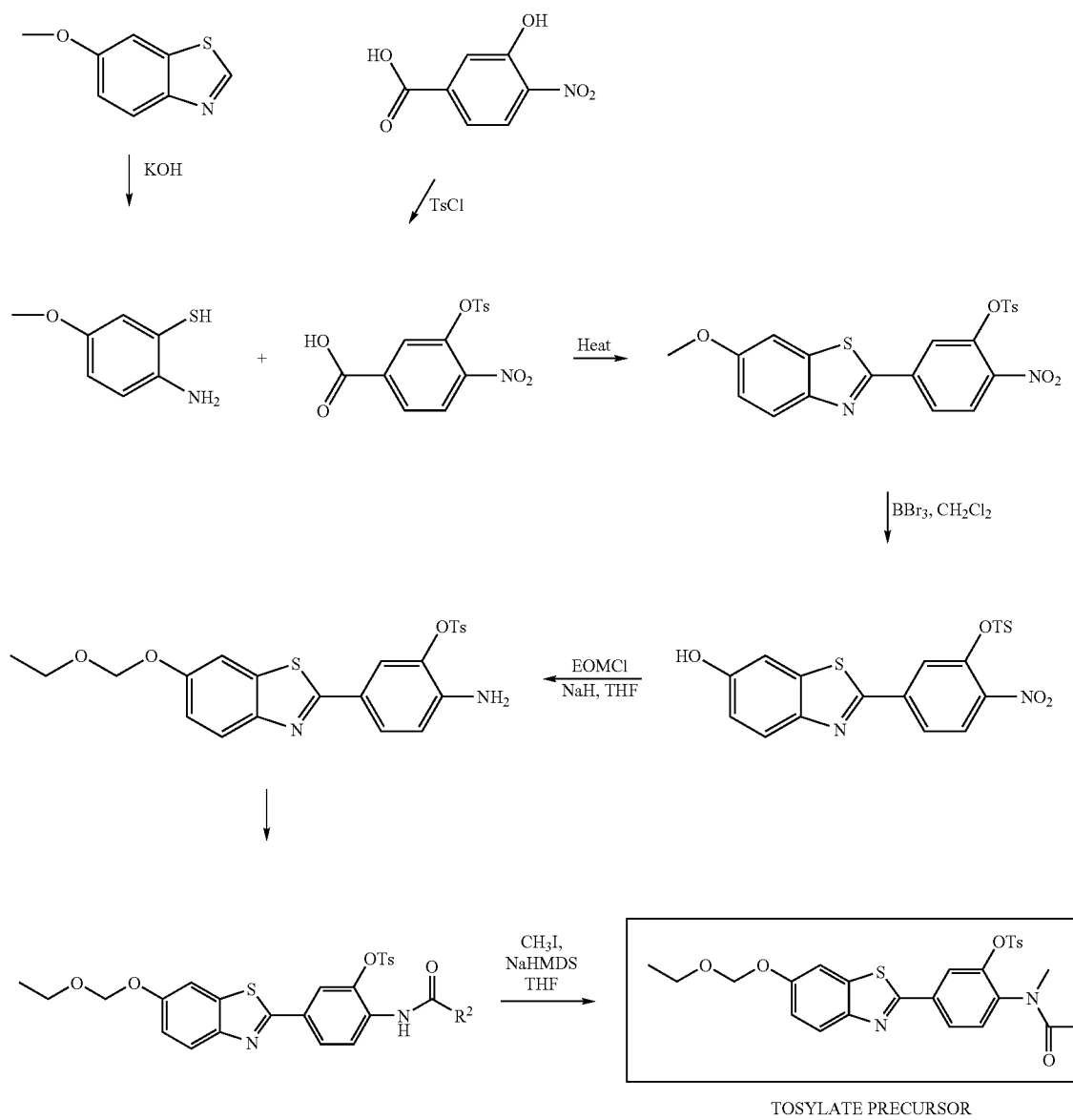
TOSYLATE PRECURSOR

Scheme 5

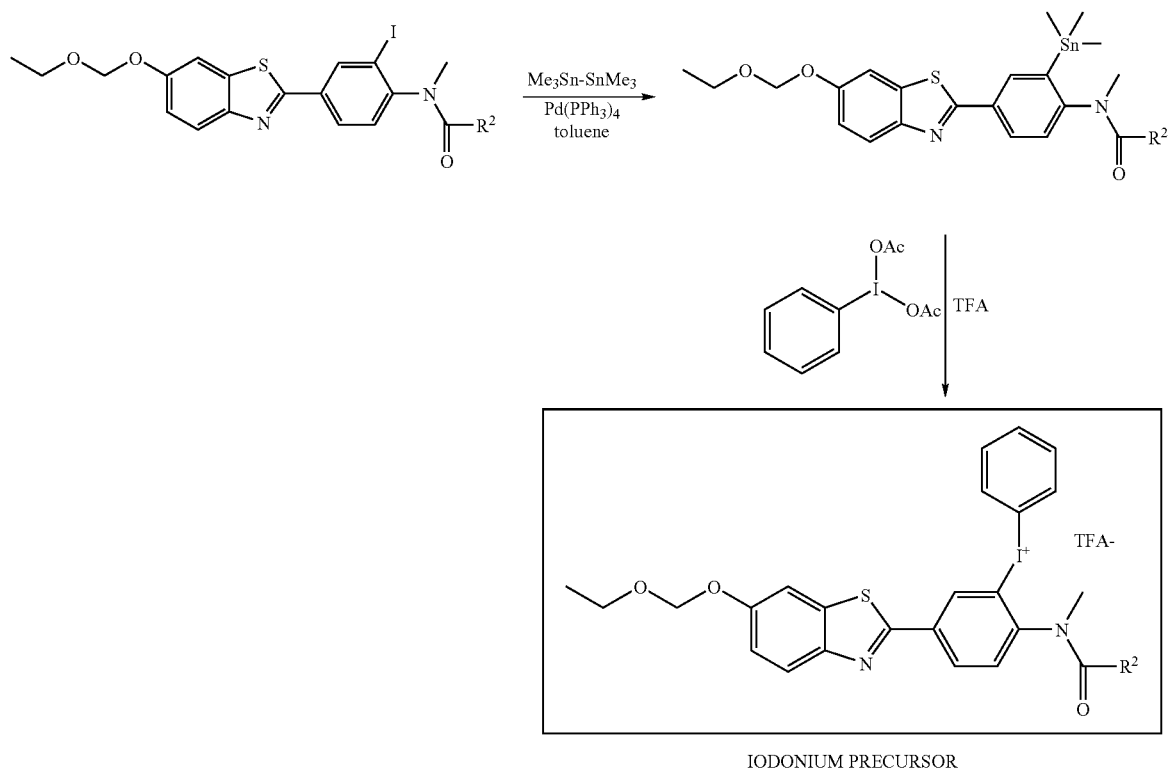

IODONIUM PRECURSOR

Compounds of formula (II), (IIa), and (IIb) wherein $R^3$ is $-N_2^+$ may be prepared from the corresponding compound wherein $R^3$ is nitro, by reduction of the nitro group to amino, for example using hydrogen and Pd/C as catalyst and then diazotization using $NaNO_2$.

Compounds of formula (II), (IIa), and (IIb) wherein $R^3$ is $-NR^4(C_{1-6}alkyl)_2^+$ may be prepared according to Scheme 6.

Scheme 6

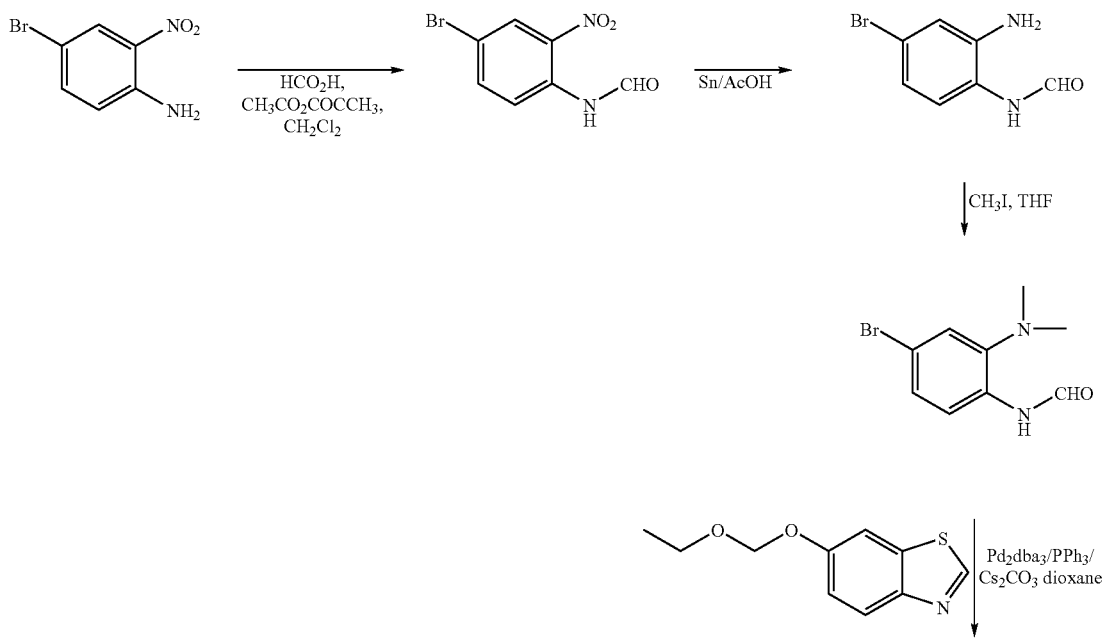

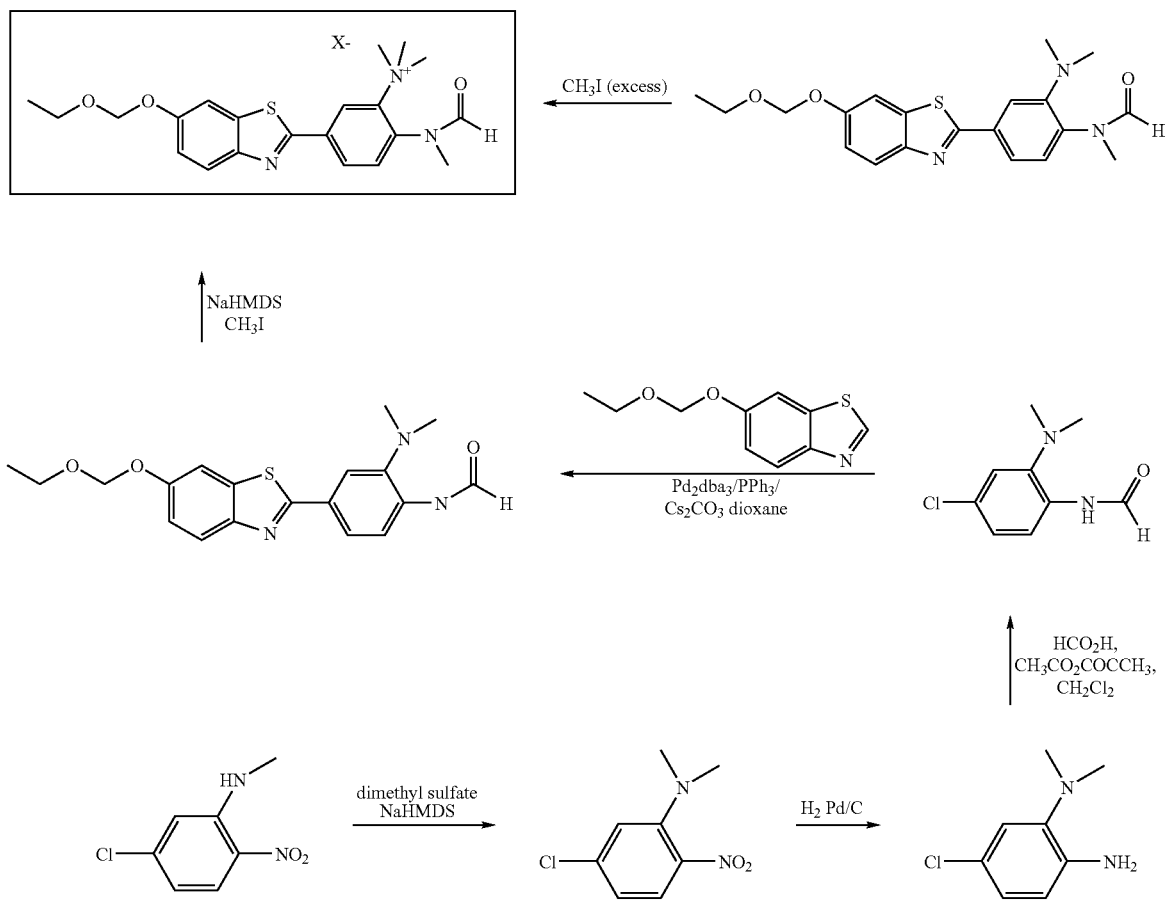

The invention is now illustrated by way of the following Examples, in which the following abbreviations are used:

| | |
|---|---|
| DMF: | N,N-dimethylformamide |
| DCM: | dichloromethane |
| EOMCl: | ethoxymethoxychloride |
| DMAP: | dimethylaminopyridine |
| RT: | room temperature |
| THF: | tetrahydrofuran |
| IMS: | industrial methylated spirits |
| M.p.: | melting point |
| eq.: | equivalents |
| EtOAc: | ethyl acetate |
| QMA: | quaternary ammonium |
| HPLC: | high performance liquid chromatography |
| mL or ml: | milliliter(s) |
| TLC: | thin layer chromatography |
| v/v: | volume/volume |
| NMR: | nuclear magnetic resonance |
| MS: | mass spectrometry |

EXAMPLE 1

Synthesis of 2-[3-nitro-4-(methylformylamino)phenyl]-6-ethoxymethoxybenzothiazole

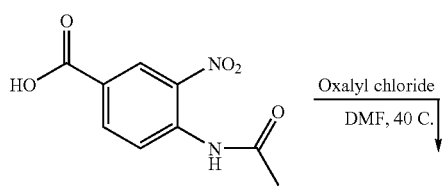

1

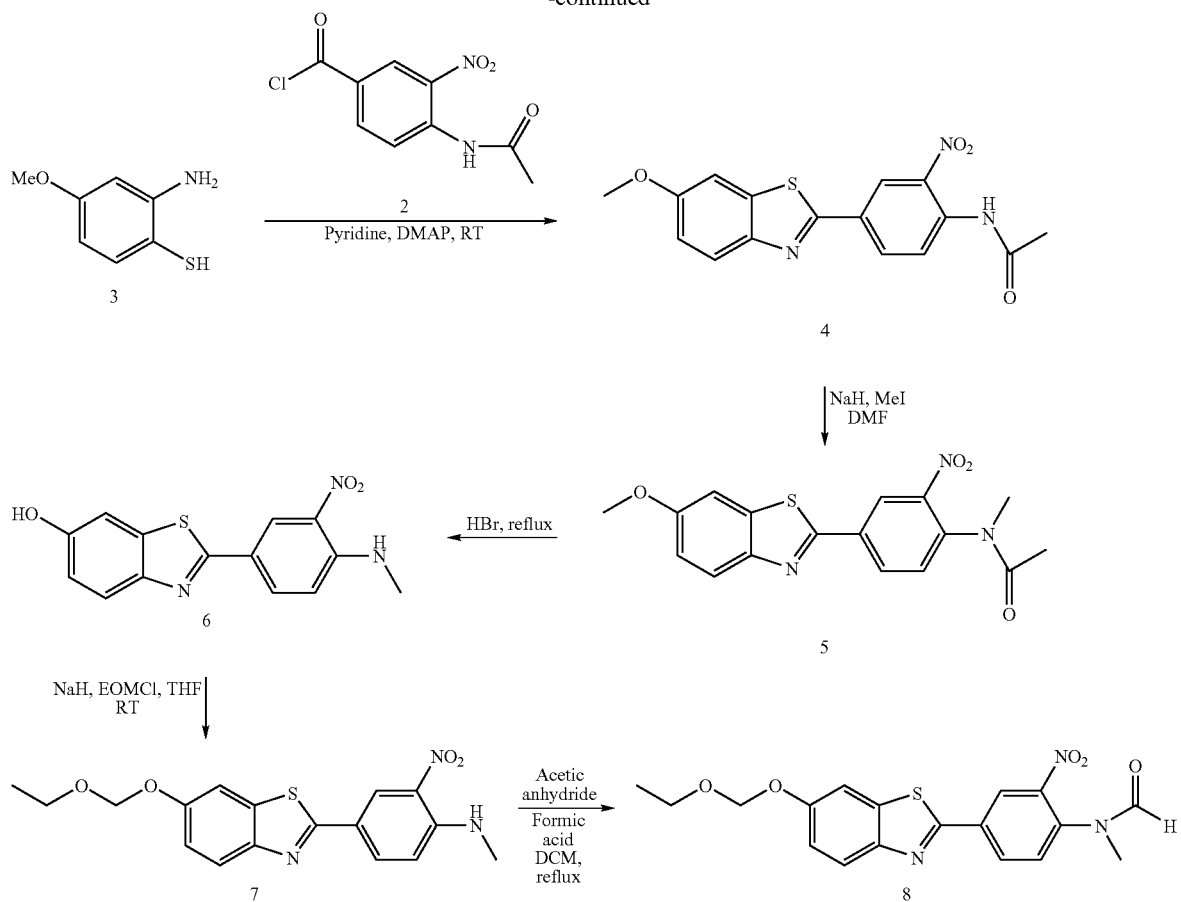

EXAMPLE 1(i)

4-Acetamido-3-nitrobenzoyl chloride (2)

4-Acetamido-3-nitrobenzoic acid 1 (Alfa Aesar, 5.6 g, 25 mmol), oxalyl chloride (4.76 g, 38 mmol), chloroform (50 ml), DMF (few drops) were stirred at 40° C. for 3 hours. The solvent was removed in vacuo to give a yellow solid that was used in the next step without further purification.

EXAMPLE 1 (ia)

5-methoxy-2-aminobenzenethiol (3)

2-Amino-6-methoxy-benzothiazole 10 g (55.6 mmol) was suspended in 25% aqueous potassium hydroxide and the mixture heated under reflux for 24 h. The pale yellow solution was cooled and acidified to pH 6 with firstly aqueous 6N HCl then acetic acid. The precipitated solid was filtered, washed with water (3×100 ml), dried (high vac.) to afford the desired material as a pale yellow powder 8.18 g, 95%.

EXAMPLE 1(ii)

2-(4-Acetamido-3-nitrophenyl)-6-methoxybenzothiazole (4)

5-Methoxy-2-aminobenzenethiol 3 (3.88 g, 25 mmol), pyridine (100 ml), and DMAP (few crystals) were stirred at room temperature. 4-Acetamido-3-nitrobenzoyl chloride (25 mmol, as produced above) was added in one portion below 30° C. The mixture was stirred for a further 1 hour. The mixture was heated to 80° C. and stirred over the weekend. The mixture was cooled. The crystals were filtered off and washed with IMS to give 2.2 g (26% yield) of 2-(4-acetamido-3-nitrophenyl)-6-methoxybenzothiazole.

EXAMPLE 1(iii)

2-(4-N-Methylacetamido-3-nitrophenyl)-6-methoxybenzothiazole (5)

Sodium hydride (6.33 g, 157 mmol) and DMF (400 ml) were stirred at room temperature. 2-(4-Acetamido-3-nitrophenyl)-6-methoxybenzothiazole 4 (45 g, 131 mmol) was added in one portion. The mixture was stirred for 1 hour. The mixture was cooled in an ice bath and methyl iodide (23.1 g, 164 mmol) was added in one portion, the temperature stayed below 20° C.

The mixture was stirred for 3 hours, water (900 ml) was added, the mixture was filtered and washed with water. The solid was recrystallised from IMS to give 43.7 g (93% yield) of 2-(4-N-methylacetamido-3-nitrophenyl)-6-methoxybenzothiazole. M.p 168-172° C.

EXAMPLE 1(iv)

2-(4-Methylamino-3-nitrophenyl)-6-hydroxybenzothiazole (6)

A mixture of 2-(4-N-methylacetamido-3-nitrophenyl)-6-methoxybenzothiazole (58 g, 162 mmol), hydrobromic acid (500 ml, 48% aqueous solution) and hydrobromic acid (500 ml, 45% in acetic acid) were stirred at 135° C. for 5 hr. The mixture was cooled to room temperature and the solid was filtered off and washed with a little water. The solid was slurried with water and the pH adjusted to about pH10 with concentrated ammonia solution. The solid was filtered off and washed with water.

The solid was triturated with IMS (200 ml), filtered, the mixture was boiled with IMS (500 ml) then cooled to room temperature then filtered. The solid was again boiled with IMS (500 ml) then cooled to room temperature then filtered. The solid was dissolved in hot DMF (200 ml), filtered and water (100 ml) added. The solid was filtered off and washed with IMS. The solid was boiled with water (300 ml) for 5 minutes, cooled, filtered, washed with water then IMS to give 45.9 g (94% yield) of 2-(4-Methylamino-3-nitrophenyl)-6-hydroxybenzothiazole. M.p 269-272° C.

EXAMPLE 1(v)

2-[3-nitro-4-(methylamino)phenyl]-6-ethoxymethoxybenzothiazole (7)

A 3 necked 250 ml round bottom flask was dried in an oven at 80° C. overnight. A suspension of 6 (16.6 mmol, 5 g) in dry THF (180 ml) has been poured drop wise into a suspension of NaH 60% dispersion in mineral oil (33.2 mmol, 1.26 g, 2 eq) in dry THF (20 ml). Once the addition was complete neat ethoxy methyl chloride (16.6 mmol, 1.54 ml, 1 eq) was added and the reaction stirred over night. The dark brown mixture was filtrated under vacuum and the filtrate concentrated under high vacuum.

The crude product was supported onto silica and purified via flash chromatography in DCM/EtOAc: 3% EtOAc The desired fraction was isolated, concentrated under high vacuum to yield 60% of an off-red solid with 95% purity.

EXAMPLE 1(vi)

2-[3-nitro-4-(methylformylamino)phenyl]-6-ethoxymethoxy-benzothiazole (8)

All glassware was dried in an oven at 80° C. overnight.

In a 1 L three necked round bottom flask fitted with a condenser and thermometer was added acetic anhydride (15 ml, 160 mmol, 22 eq) dropwise to a solution of formic acid (160 mmol, 6 ml, 22 eq) at 0° C. The mixture was stirred for 15 minutes at 60° C.

A solution of 7 (7.2 mmol, 2.6 g) in dry DCM (310 ml) is added dropwise at 0° C. to the mixed anhydride. Stirring was continued at this temperature for one hour and the clear orange solution was stirred 5 days at 40° C.

The reaction was followed by HPLC: after 5 days 60% conversion into the desired product was observed.
HPLC Conditions:
Column Phenomenex Luna 150×4.6 nm
Flow 1 ml/minutes
Solvent: Acetonitrile (B) and Water (A)
Detection: 254-214
Gradient 5-95% of B over 8 minutes
Retention time: 9.5 minutes The clear orange solution was washed with 1N NaOH aq (3×100 ml), water (3×100 ml), dried over magnesium sulfate and concentrated under high vacuum.

The bright orange crude product was supported onto silica and purified via flash chromatography in DCM/EtOAc: 3-10% EtOAc The desired fraction was isolated, concentrated under high vacuum to yield 54.2% of an off yellow solid with 98% purity.

EXAMPLE 1(vii)

Preparation of 2-[3-[$^{18}$F]-fluoro-4-(methylamino)phenyl]-6-hydroxy-benzothiazole (11)—see Scheme below (Approach 1)

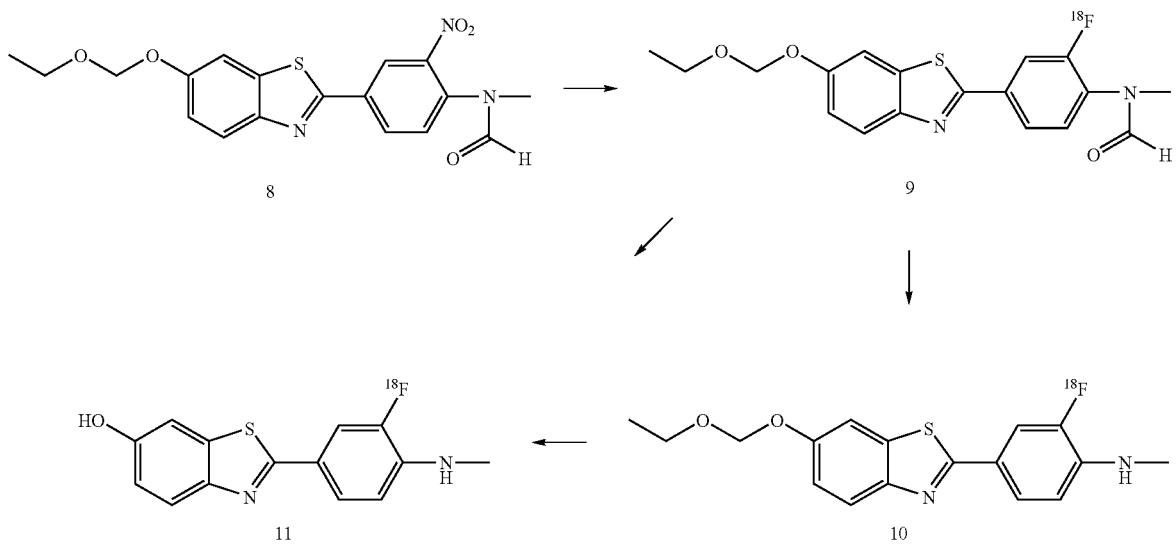

[$^{18}$F]fluoride (in 200 μL enriched 95% $^{18}$O water), 2.5 mg of Kryptofix 2.2.2 (in 0.5 mL acetonitrile) and 50 μL 0.1 M $K_2CO_3$ were added to a glassy carbon reaction vessel. The solution was then evaporated to dryness using a stream of nitrogen and heating the reaction vessel to 100° C. for 15 minutes. 2×1 mL acetonitrile was added to the reaction vessel at 5 minutes and 10 minutes respectively to aid azeotropic drying. The reaction vessel was cooled to room temperature and 2-[3-nitro-4-(methylformylamino)phenyl]-6-ethoxymethoxy-benzothiazole (8) (5.0 mg) in 1 mL anhydrous dimethyl sulfoxide was added. The reaction was sealed and heated for 10 minutes at 130° C. The crude mixture was analyzed by HPLC and TLC.

0.25 mL of 6M HCl and 0.5 mL DMSO was added to the crude reaction solution of 2-[3-[$^{18}$F]-fluoro-4-(methylformylamino)phenyl]-6-ethoxymethoxy-benzothiazole (9) and heated at 125° C. for 10 minutes. The reaction was then cooled to room temperature and neutralized using 2M sodium acetate resulting in the synthesis of 2-[3-[$^{18}$F]-fluoro-4-(methylamino)phenyl]-6-hydroxy-benzothiazole (11). The crude mixture was analyzed by HPLC and TLC.

HPLC Purification and Formulation.

2-[3-[$^{18}$F]-fluoro-4-(methylamino)phenyl]-6-hydroxy-benzothiazole (11) was purified by HPLC using a Phenomenex Prodigy ODS preparative. 10 um 250 mm×10 mm (part no. 00G-4088-N0) preparative column (the column is eluted with 40/60 acetonitrile/triethylamine phosphate buffered solution pH 7 (v/v)). The control method is 0-15 minutes 5 ml/minute, 15.5-39.9 minutes 8 ml/minute, 40 minutes 5 ml/minute. The product elutes with a retention time of 22-23 minutes (in a volume of 8 mL).

The HPLC purified "cut" was diluted to 50 mL with addition of distilled water. The product was then "trapped" onto a C8-sep-pak cartridge and then eluted off the cartridge with 1 mL ethanol. The ethanol was then removed under vacuum and the final product formulated in 10% ethanol/90% phosphate buffered saline.

EXAMPLE 2

Preparation of 2-[3-[$^{18}$F]fluoro-4-(methylamino) phenyl]-6-hydroxy-benzothiazole (11)—see Scheme above (Approach 2)

EXAMPLE 2(i)

Preparation of [K/K2.2.2]$^+$ $^{18}$F (using enriched 95% $^{18}$O water).

After irradiation, the target content was passed through a column packed with QMA resin. The column was purged with helium for 5 minutes. The [$^{18}$F]fluoride adsorbed on the resin was eluted into a reaction vial with 4 ml of a 96:4 (by volume) acetonitrile-water mixture containing 19.1 mg of Kryptofix 2.2.2 and 2.9 mg of $K_2CO_3$; the solution was then evaporated and co-evaporated with anhydrous acetonitrile (2×1 ml) to dryness in a nitrogen stream at 110° C.

EXAMPLE 2(ii)

Preparation of 2-[3-[$^{18}$F]-fluoro-4-(methylformylamino)phenyl]-6-ethoxymethoxy-benzothiazole (9) and 2-[3-[$^{18}$F]-fluoro-4-(methylamino)phenyl]-6-ethoxymethoxy-benzothiazole (10)

A solution of 2-[3-nitro-4-(methylformylamino)phenyl]-6-ethoxymethoxy-benzothiazole (8) (3.0 mg) in anhydrous acetonitrile (0.1 ml) was added to a solution of [K/K2.2.2]$^{+18}$F$^-$ in anhydrous acetonitrile (0.25 ml). The reaction mixture was heated at 150° C. for 15 minutes. The crude mixture was analyzed by analytical HPLC.

EXAMPLE 2(iii)

Conversion of 2-[3-[$^{18}$F]-fluoro-4-(methylformylamino)phenyl]-6-ethoxymethoxy-benzothiazole (9) to 2-[3-[$^{18}$F]-fluoro-4-(methylamino)phenyl]-6-ethoxymethoxy-benzothiazole (10)

About 0.2 ml of the previous reaction mixture was added to a solution of NaH (3.2 mg) in anhydrous acetonitrile (0.2 ml) at room temperature. The resulted mixture was heated at 100° C. for 5 minutes. The crude mixture was analyzed by analytical HPLC.

Preparation of 2-[3-[$^{18}$F]-fluoro-4-(methylamino) phenyl]-6-hydroxy-benzothiazole (11)

A solution of concentrated HCl in MeOH (1:2) (0.25 ml) was added to the previous reaction mixture and heated at 100° C. for 5 minutes. The crude mixture was analyzed by analytical HPLC.

EXAMPLE 3

Comparative [$^{18}$F]-Fluorination of Different Precursors

Radiofluoridation of various benzothiazole precursor compounds using methods analogous to those described in Example 1(vii) gave the results shown in Table 1. Crude yield was calculated from radiochemical purity measured by HPLC, corrected for product lost by retention on HPLC and in the reaction vessel.

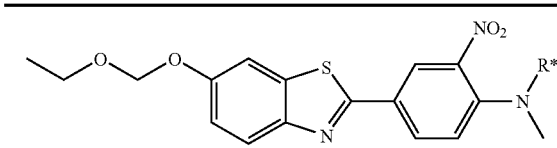

| Precursor; R* = | |
|---|---|
| H | <5% crude Yield |
| 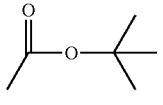 | <5% crude Yield |
| 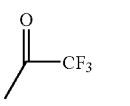 | <5% crude Yield |
| 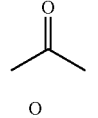 | <5% crude Yield |
|  | Current labeling 25-30% incorporation |

EXAMPLE 4

Automated synthesis of 2-[3-[$^{18}$F]-fluoro-4-(methylamino)phenyl]-6-hydroxy-benzothiazole (11)

The reagent positions of a TRACERlab FX$_{FN}$ (GE Healthcare Ltd) automatic synthesiser unit were loaded with the following solutions:

i. 0.1 M potassium carbonate in water (0.5 mL)
ii. 0.13M Kryptofix 2.2.2 in acetonitrile (0.5 mL)
iii. Precursor solution: 0.1 M 2-[3-nitro-4-(methylformylamino)phenyl]-6-ethoxymethoxy-benzothiazole (8) in DMSO (1.0 mL)
iv. 4M hydrochloric acid (0.25 mL)
v. ethanol (1.0 mL)
vi. 0.01M phosphate buffer, pH 7.4 (13.1 mL)

When a solution of [$^{18}$F]fluoride in [$^{18}$O]-enriched water (121 MBq) had been loaded into the synthesiser's starting position the operator initiated the programme causing the following sequence of events to take place.

The fluoride solution passed through a QMA cartridge (pre-conditioned with 10 mL of 0.5M aqueous potassium carbonate and 20 mL of water) trapping the fluoride and sending the enriched water to waste. The QMA cartridge was then eluted with the 0.1 M potassium carbonate solution to recover the fluoride and the eluant was directed to the reactor vessel. The solution of Kryptofix 2.2.2 was added to the reactor and the mixture was heated at 60° C. for 5 minutes under a gentle flow of nitrogen at reduced pressure. The temperature was then raised to 120° C. and held under vacuum for 7 minutes to dry the contents of the reactor. After cooling to 50° C., the Precursor solution was added to the reactor and the temperature was raised to 135° C. for 10 minutes. This step allows [$^{18}$F]fluoride to be incorporated into the organic molecule. The solution was cooled to 50° C. and the 4M hydrochloric acid was added. The mixture was heated to 125° C. for 5 minutes to cause deprotection of the intermediate compound and, after cooling to 40° C., the crude product solution was injected onto a Phenomenex Gemini C18 HPLC column (250×21.2 mm, 5 μm). The column was eluted with 6 mM hydrochloric acid-acetonitrile mixture (53:47, v:v) at 10 mL/min. The desired product was identified by radio-detection and collected by cutting. The obtained solution was diluted with water (150 mL) and passed through a Sep-Pak® Plus C8 cartridge (pre-conditioned with 10 mL ethanol and 10 mL water) so that the product was retained on the cartridge. The cartridge was eluted with ethanol into the product vial which contained propylene glycol (0.9 mL). Phosphate buffer was also passed through the cartridge into the product vial to give the formulated product. Yield of the product was 10.8% (non-corrected, based on [$^{18}$F] starting activity) and the radiochemical purity was >99%.

EXAMPLE 5

Alternative synthesis of 2-[3-nitro-4-(methylformylamino)phenyl]-6-ethoxymethoxy-benzothiazole (8)

EXAMPLE 5(i)

Synthesis of 4-Chloro-N-(4-hydroxy-phenyl)-3-nitro-benzamide

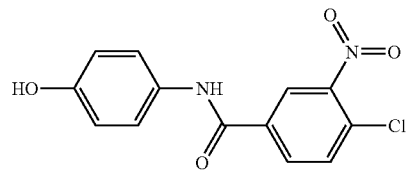 [SMILES: O=C(Nc1ccc(O)cc1)c1ccc(Cl)c([N+](=O)[O-])c1]

4-Amino-phenol (12 g, 0.11 mol, Acros and Aldrich) was dissolved under an inert atmosphere, with stirring, in dry DMF (50 ml) and cooled in an ice-bath. Triethylamine (TEA, 11 g, 0.11 mol) was added and stirring continued for 1 hour. 4-Chloro-3-nitro-benzoyl chloride (22.2 g 0.1 mol, Acros and Aldrich) was added slowly and stirred overnight. The precipitated triethylamine.hydrochloride salt was filtered off and DMF removed under reduced pressure. The residue was extracted with EtOAc (3×100 ml) and citric acid (1M, 3×100 ml). The organic phase was dried with magnesium sulphate, filtered and evaporated to dryness under reduced pressure. The title product was recrystallised from methanol/water (1:1, 250 ml), yield 85%, and analysed by NMR and MS.

EXAMPLE 5(ii)

Synthesis of 4-Chloro-N-(4-ethoxymethoxy-phenyl)-3-nitro-benzamide

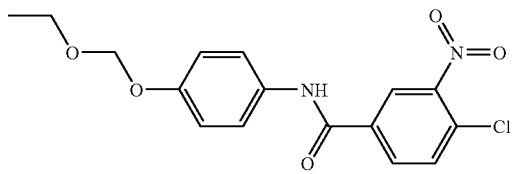 [SMILES: CCOCOc1ccc(NC(=O)c2ccc(Cl)c([N+](=O)[O-])c2)cc1]

4-Chloro-N-(4-hydroxy-phenyl)-3-nitro-benzamide (14.6 g, 0.05 mol) was placed in an oven dried 2-necked 500 ml round-bottomed flask and flushed with N$_2$. Enough Dimethoxyethane (DME, 100 ml) was added to dissolve the amide. The mixture was cooled in ice bath and sodium hydride (NaH, 50% in oil, 3.6 g total, 0.075 mol) added in small portions with vigorous stirring. An hour after addition was complete, chloromethoxy-ethane (7.13 g, 0.075 mol, commercially available) was added drop wise via a pressure-equalising dropping funnel. The reaction was followed by TLC (dichloromethane, DCM:methanol, MeOH, 95:5). The reaction mixture was poured into ice water and extracted with EtOAc (3×50 ml). The organic phase was dried (MgSO$_4$) and evaporated under reduced pressure. The crude product was recrystallised form Hexane/ethyl acetate, 1:4. to give 81% of the title compound.

EXAMPLE 5(iii)

Synthesis of 4-Chloro-N-(4-ethoxymethoxy-phenyl)-3-nitro-thiobenzamide

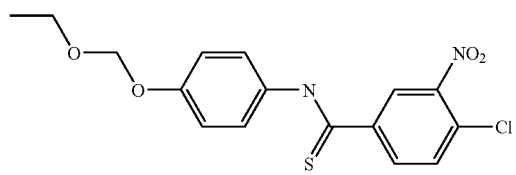 [SMILES: CCOCOc1ccc(NC(=S)c2ccc(Cl)c([N+](=O)[O-])c2)cc1]

4-Chloro-N-(4-ethoxymethoxy-phenyl)-3-nitro-benzamide (3.5 g, 10 mmol), phosphorus pentasulfide $P_4S_{10}$ (0.81 g, 1.83 mmol, commercially available), hexamethyldisiloxane (2.7 g, 16.7 mmol, commercially available) and toluene (10 ml) were added into a 100 ml round-bottomed flask and flushed with nitrogen. The mixture was heated under reflux and was followed by TLC. Heating continued until no more starting benzamide remained. Microwave heating can also be used. The reaction mixture was cooled to room temperature. Potassium carbonate solution (4 ml of 5.3M solution) was added. Acetone (10 ml) was added and the mixture stirred for 1 hour in an ice bath, the extracted with toluene and water. The organic phase was dried ($MgSO_4$) and toluene removed under reduced pressure and purified by flash chromatography with ethyl acetate/hexane as eluent.

EXAMPLE 5 (iiia)

Alternative Thioamidation procedure: synthesis of N-(4-Benzyloxy-phenyl)-4-chloro-3-nitro-thiobenzamide

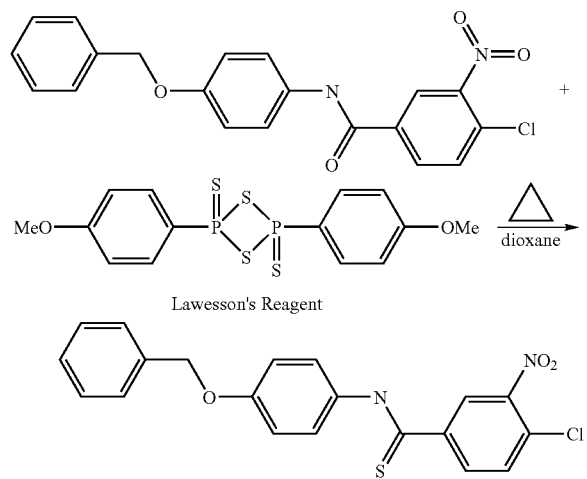

Lawesson's Reagent

N-(4-Benzyloxy-phenyl)-4-chloro-3-nitro-benzamide (19.15 g, 50 mmol), Lawesson reagent (11 g, 27 mmol, commercially available) and dioxane (150 ml) were stirred together and heated under reflux for 4 h. When no more starting amide was present, as showed by TLC, the reaction mixture was cooled and the solvent removed under reduced pressure. The crude product was dissolved in minimum boiling toluene to recrystallise. The purified product was filtered and washed with cold toluene and cold hexane to give the thioamide, in 77% yield.

EXAMPLE 5(iva)

Synthesis of 6-benzyloxy-2-(4-chloro-3-nitro-phenyl)-benzothiazole

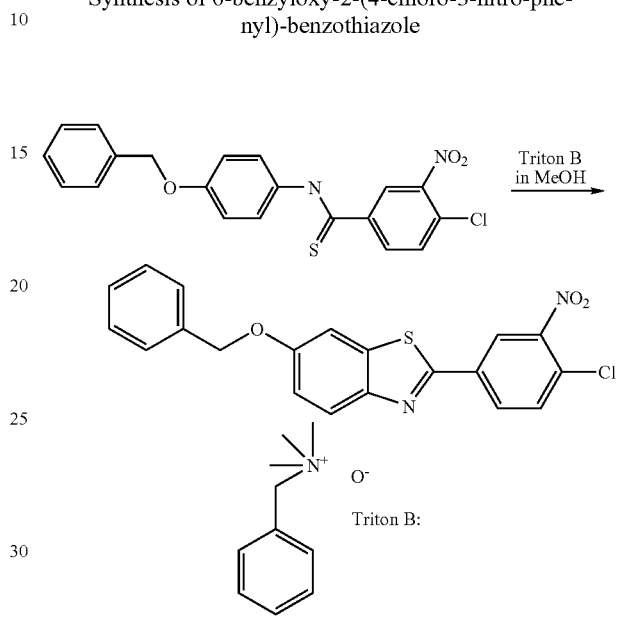

Triton B:

N-(4-Benzyloxy-phenyl)-4-chloro-3-nitro-thiobenzamide (2 g, 5 mmol) was dissolved in methanol (100 ml). Sodium hydroxide (1.6 g in 5 ml water) was added followed by Triton B (2.1 ml, 5 mmol, commercially available). The mixture was cooled in an ice-bath. Potassium ferri(III) cyanide (13.2 g in 50 ml water) was added drop wise with vigorous stirring. The reaction mixture was allowed to warm up overnight and was further warmed to 130° C. for 1 hour. The reaction mixture was cooled and extracted with ethyl acetate/water. The organic phase dried and the solvent removed under reduced pressure. The product, compound was purified by flash chromatography with Hexane/Ethyl acetate as eluent.

EXAMPLE 5(iv)

Synthesis of 6-ethoxymethoxy-2-(4-chloro-3-nitro-phenyl)-benzothiazole

Using methods analogous to those described in Example 5(iva), the thiobenzamide prepared in Example 5(iii) may be cyclised to form the title compound.

EXAMPLE 5(v)

Synthesis of 6-benzyloxy-2-(4-methylamino-3-nitro-phenyl)-benzothiazole and 6-ethoxymethoxy-2-(4-methylamino-3-nitro-phenyl)-benzothiazole (7)

The compounds of Examples 5(iva) and 5(iv) respectively, are reacted with methylamine in aqueous solution, heating to 130° C., for example in a microwave oven. The reaction mixture is extracted with ethyl acetate/water and the organic phase is dried, before removing the solvent under reduced pressure. The title products are purified by flash chromatography using hexane/ethyl acetate.

EXAMPLE 5(vi)

Synthesis of 2-[3-nitro-4-(methylformylamino)phenyl]-6-benzyloxy-benzothiazole and 2-[3-nitro-4-(methylformylamino)phenyl]-6-ethoxymethoxy-benzothiazole (8)

The title compounds are prepared from the compounds of Example 5(v) respectively using formylation methods analogous to those described in Example 1 (vi).

EXAMPLE 6

Alternative synthesis of 2-[3-nitro-4-(methylformylamino)phenyl]-6-ethoxymethoxy-benzothiazole (8)

The synthesis is performed, by analogy to Example 5, but starting with 4-amino-3-chloro-phenol to prepare 6-ethoxymethoxy-2-(4-chloro-3-nitro-phenyl)-benzothiazole via 4-Chloro-N-(4-hydroxy-2-chloro-phenyl)-3-nitro-benzamide, 4-Chloro-N-(4-ethoxymethoxy-2-chloro-phenyl)-3-nitro-benzamide, and 4-Chloro-N-(4-ethoxymethoxy-2-chloro-phenyl)-3-nitro-thiobenzamide. Cyclisation of 4-chloro-N-(4-ethoxymethoxy-2-chloro-phenyl)-3-nitro-thiobenzamide to form 6-ethoxymethoxy-2-(4-chloro-3-nitro-phenyl)-benzothiazole is performed using literature methods, for example Bowman et al Tetrahedron, 47(48), 10119-10128 (1991); Couture and Glandclaudon, Heterocycles, 22(6) 1984; Hutchinson et al, Tetrahedron Lett. 2000, 41(3), 425-8. Subsequent methylation and formylation are then performed as described in Example 5.

What is claimed is:
1. A process for preparation of a compound of formula (I):

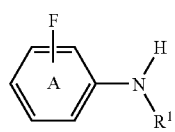
(I)

wherein phenyl ring A is optionally substituted by 1 to 4 substituents;
$R^1$ is $C_{1-6}$alkyl, $C_{2-6}$alkenyl, or $C_{2-6}$alkynyl;
which comprises:
(i) reaction of a corresponding compound of formula (II):

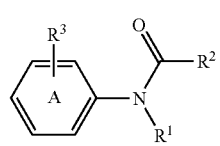
(II)

wherein ring A is optionally substituted as defined for the compound of formula (I); $R^2$ is hydrogen, $C_{1-10}$alkyl, $C_{1-10}$haloalkyl, $C_{6-14}$aryl, $C_{6-14}$arylalkyl, or —(CH$_2$CH$_2$O)$_q$—CH$_3$ wherein q is an integer of from 1 to 10;
$R^1$ is as defined for the compound of formula (I); and
$R^3$ is a leaving group;

with fluoride or an isotope thereof to give a compound of formula (III), whereby said leaving group is displaced by said reaction with fluoride or an isotope thereof

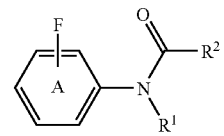
(III)

wherein $R^1$ and $R^2$ are as defined for the compound of formula (I) and phenyl ring A is substituted as defined for the compound of formula (I); followed by step (ii) and optionally step (iii) in any order
(ii) conversion of group —C(O)R$^2$ to hydrogen,
(iii) removal of any protecting groups.

2. A process according to claim 1 wherein phenyl ring A is optionally substituted by 1 to 4 organic substituents selected from group consisting of fluoro, chloro, bromo, iodo, cyano, nitro, —R, —OR, —OC(O)R, —C(O)R, —SR, —NR$_2$, —C(O)NR$_2$ wherein R at each occurance is selected from $C_{1-6}$alkyl, $C_{2-6}$alkenyl, $C_{2-6}$alkynyl, $C_{1-6}$alkoxy-$C_{1-6}$alkyl, $C_{1-6}$haloalkyl, $C_{2-6}$haloalkenyl, $C_{2-6}$haloalkynyl, $C_{1-6}$haloalkoxy—$C_{1-6}$alkyl, $C_{5-12}$aryl, $C_{5-12}$ hetaryl wherein said aryl and hetaryl substituents may be further substituted by the non-aryl and non-hetaryl substituents listed for phenyl ring A, and a protected derivative of any thereof.

3. A process according to claim 1 wherein said fluoride of step (i) is [18F]fluoride to produce the compound of formula (I) wherein the fluoro group is [$^{18}$F]fluoro.

4. A process according to claim 1 wherein $R^3$ in the compound of formula (II) is selected from the group consisting of:
nitro,
—N$_2$$^+$,
chloro,
bromo,
iodo,
—NR$^4$(C$_{1-6}$alkyl)$_2$$^+$ wherein $R^4$ is $C_{1-6}$alkyl or a group of formula (X):

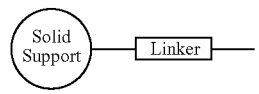
(X)

—OSO$_2$R$^5$ wherein $R^5$ is selected from $C_{1-6}$alkyl, $C_{1-6}$haloalkyl, aryl, and a group of formula (X) as defined above; and

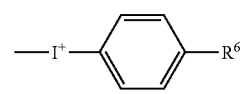

wherein $R^6$ is selected from hydrogen, $C_{1-6}$alkyl, halo, nitro, and a group of formula (X) as defined above.

5. A process according to claim 4 wherein $R^3$ is selected from the group consisting of:
nitro,
—N$_2$$^+$,
chloro,
bromo,
iodo, —NR$^4$(C$_{1-6}$alkyl)$_2$$^+$ wherein R$^4$ is C$_{1-6}$alkyl ;
—OSO$_2$R$^5$ wherein R$^5$ is selected from C$_{1-6}$alkyl, C$_{1-6}$haloalkyl; and

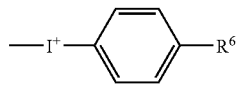

wherein R$^6$ is selected from hydrogen, C$_{1-6}$alkyl, halo, and nitro.

6. A process according to claim 4 wherein R$^3$ is nitro.

7. A process according to claim 1 wherein R$^1$ is C$_{1-6}$alkyl.

8. A process according to claim 1 wherein R$^2$ in the compound of formula (II) is hydrogen or C$_{1-6}$alkyl.

9. A process according to claim 1 wherein step (ii) is effected by reaction with a non-nucleophilic base in an aprotic solvent and at elevated temperature of about 40° C. to 120° C.

* * * * *